United States Patent [19]
Burkinshaw et al.

[11] Patent Number: 6,013,081
[45] Date of Patent: Jan. 11, 2000

[54] APPARATUS AND METHOD FOR ANTERIOR AND POSTERIOR REFERENCED SIZING AND DISTAL FEMUR RESECTION

[75] Inventors: Brian D. Burkinshaw; Donald W. Dye, both of Pflugerville, Tex.

[73] Assignee: Sulzer Orthopedics Inc., Austin, Tex.

[21] Appl. No.: 09/149,989

[22] Filed: Sep. 9, 1998

[51] Int. Cl.[7] .................................................. A61B 17/15
[52] U.S. Cl. ............................... 606/88; 606/96; 606/102
[58] Field of Search ............................ 606/88, 89, 87, 606/86, 96, 102, 82

[56] References Cited

U.S. PATENT DOCUMENTS

| | | | |
|---|---|---|---|
| 5,417,694 | 5/1995 | Marik et al. | 606/88 |
| 5,486,178 | 1/1996 | Hodge | 606/82 |
| 5,562,675 | 10/1996 | McNulty et al. | 606/88 |
| 5,569,261 | 10/1996 | Marik et al. | 606/88 |
| 5,624,444 | 4/1997 | Wixon et al. | 606/88 |
| 5,662,656 | 9/1997 | White | 606/88 |
| 5,688,279 | 11/1997 | McNulty et al. | 606/88 |
| 5,688,281 | 11/1997 | Cripe et al. | 606/88 |

FOREIGN PATENT DOCUMENTS

| | | |
|---|---|---|
| 0 340 176 A2 | 2/1989 | European Pat. Off. . |
| 340176 | 11/1989 | European Pat. Off. . |
| 0 380 451 A2 | 1/1990 | European Pat. Off. . |
| 380451 | 8/1990 | European Pat. Off. . |

*Primary Examiner*—Michael Buiz
*Assistant Examiner*—David O. Reip
*Attorney, Agent, or Firm*—Philip S. Lyren; Kenneth S. Barrow

[57] ABSTRACT

Apparatus for distal femur sizing and resection includes an adjustable sizer cut guide device formed by a sizer member, a femoral cut guide and a slide stone. The slide stone is provided to receive an intramedullary rod inserted into the femur. A first member and a second member are sequentially, removably attachable to the adjustable sizer cut guide device. The first member is an adjustable reference device provided for referencing. The second member is a distal cut guide which is attached to the adjustable sizer cut guide device after removal of the reference device, to position the distal cut guide on the femur. Readable scales on the adjustable sizer cut guide device and on the adjustable reference device, are matched to provide a size reference for a femoral prosthesis.

25 Claims, 15 Drawing Sheets

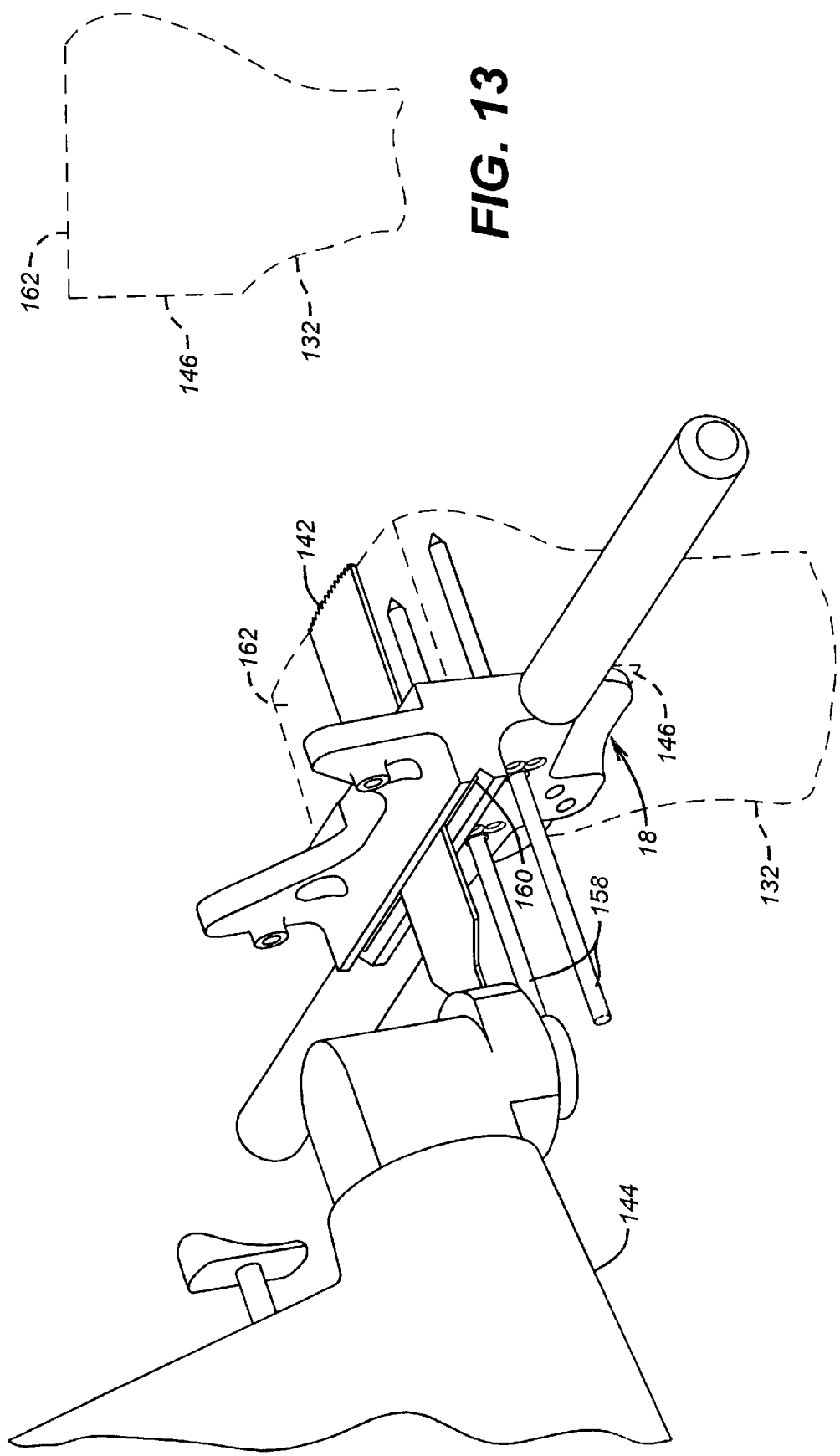

APPARATUS AND METHOD FOR ANTERIOR AND POSTERIOR REFERENCED SIZING AND DISTAL FEMUR RESECTION

BACKGROUND

The disclosures herein relate generally to orthopedic implant systems and more particularly to an anterior or posterior referencing instrument including an anterior femoral cutting guide and a distal femoral cutting guide.

There are many problems encountered by orthopedic surgeons when attempting to properly size and reset the distal femoral articulating surfaces in preparation for total knee arthroplasty. The intramedullary canal is located for proper centering of an intramedullary rod to be inserted therein. Anterior or posterior referencing are used to properly establish cutting planes for receiving a properly sized femoral reconstruction component. In anterior referencing, anterior-posterior placement of the femoral component is based on the anterior cortex as a primary point of reference. In posterior referencing, anterior-posterior placement of the femoral component is based on the posterior femoral condyles as a primary point of reference.

Numerous approaches have been taken to achieve accurate sizing for a knee prosthesis. U.S. Pat. No. 5,417,694 and U.S. Pat. No. 5,569,261, each disclose a distal femoral cutting instrument which includes an intramedullary rod for referencing the patient's intramedullary canal. A valgus block with a flat reference surface mounts to the intramedullary rod at a bore of the valgus block. The bore of the block has a slant with respect to the flat reference surface on the valgus block. The reference surface defines a line that is normal to the mechanical axis of the patient while the bore of the valgus block tracks the patient's biomechanical axis. A distal femoral cutting block removably attaches to the valgus block and provides a flat cutting guide surface for shaping the patient's distal femur. The valgus block, intramedullary rod, and a stylus are removed as a unit before shaping of the distal femur. An indexing system includes a gauge having a series of openings corresponding to "anterior" referencing and to "posterior" referencing. During anterior referencing, the gauge allows the surgeon to select the next smaller size prosthesis if the size falls in between available sizes. In posterior referencing, the gauge allows the surgeon to select the next larger size prosthesis if the gauge measures a size that falls in between available sizes.

In U.S. Pat. No. 5,486,178, a femoral preparation instrumentation system and method employs a multi-purpose sizing guide for placement at the distal femur, secured to an intramedullary alignment rod seated within the femur, enabling the determination of the appropriate size for the femoral knee prosthesis to be implanted and the setting of the axial rotational position of the femoral knee prosthesis, and providing for the accomplishment of preliminary posterior condylar cuts and the location of a distal femoral resection guide at the distal femur, while the sizing guide remains in place at the distal femur.

U.S. Pat. No. 5,624,444 discloses a set of instruments and method for use in knee replacement surgery, specifically to make the necessary femoral resections. The set of instruments allows the necessary femoral resections to be performed with fewer instruments, and with fewer necessary steps for the surgeon to take. The set of instruments includes a three-dimensional jig which references the anterior and posterior femoral condyles to allow determinations as to alignment, placement, and prosthesis size before any bone cuts are made.

U.S. Pat. No. 5,662,656 discloses instrumentation for and a method of sizing the end of a distal femur, and resecting the distal femur. An instrument body construct is provided with an instrument body and a valgus module for attachment to the instrument body. The instrument body construct has a distal aspect abutting surface with a planar face for abutting the distal aspect of a distal femur at a fixed angle to the longitudinal axis of the distal femur, having a posterior aspect abutting surface with a planar face for abutting the posterior aspect of the distal femur, and having a passageway therethrough. An anterior feeler gauge is provided for attachment to the instrument body construct and for contacting a portion of the anterior aspect of the distal femur to indicate the anterior-to-posterior size of the distal femur. A resection guide is provided for attachment to the instrument body construct for guiding a bone resection tool to resect the distal femur. The resection guide may have a first position for guiding the bone resection tool to perform an anterior femoral resection, and a second position for guiding the bone resection tool to perform a distal femoral resection.

In U.S. Pat. No. 5,688,279, an alignment guide for positioning a saw guide at a predetermined position on the distal femur is placed on the femur and receives an intramedullary rod inserted in the femur. The guide has an arm for coupling the saw guide block. The guide includes an intercondylar saddle that engages the intercondylar notch of the femur to align the saw guide at a predetermined position proximal to the intercondylar notch.

U.S. Pat. No. 5,688,281 discloses an intramedullary alignment guide and method for use thereof for accurately preparing and shaping the distal femur end surface to receive a knee prosthesis. The guide references the femur intramedullary canal to ensure that a distal femoral resector is properly positioned at a selected angle with respect to a patient's mechanical axis. The intramedullary alignment guide includes an opening for inserting an intramedullary rod therethrough and into the intramedullary canal of a patient. The guide includes an adjustment mechanism which allows a surgeon to quickly and easily deflect an attached distal femoral resector into a desired angular displacement with respect to intramedullary canal. The distal femoral resector is angled with respect to the intramedullary canal so that a cut can be made in a patient's distal femur end which is perpendicular with the patient's mechanical axis. The guide can be used on patients having various anatomies, and in operations involving both the right and left legs. A slighting tool is also disclosed which allows a surgeon to externally verify that the distal femoral resector is properly aligned with the patient's mechanical axis.

Therefore, what is needed is an instrument which permits anterior and posterior referenced sizing and guide slots for making both the anterior reference femoral cut and the distal femoral cut thus providing a first and a second locating datum for subsequent use of a chamfer speed block.

SUMMARY

One embodiment, accordingly, provides an instrument which provides distal femoral sizing for a femoral prothesis, and guides the cutting of the anterior and the distal femoral reference cuts. To this end, an apparatus for distal femur sizing and resection includes a sizer member, a slide member movably mounted in the sizer member, and a femoral cut guide movably engaged with the sizer member. A first member and a second member are sequentially removably attachable to the femoral cut guide. The first member is a reference device attached to the femoral cut guide for referencing, and the second member is a distal cut guide attachable to the femoral cut guide subsequent to removal of the reference device, to position the distal cut guide on the femur.

A principal advantage of this embodiment is that the device and technique consolidate several time consuming steps into a compact procedure utilizing a multi-purpose instrument, to accurately locate and make the anterior femoral reference cut and the distal femoral reference cut.

BRIEF DESCRIPTION OF THE DRAWINGS

FIG. 12 is an isometric view illustrating another reference cut being made using an embodiment of a portion of the device engaged with the distal femur.

FIG. 13 is a side view of the distal femur including the completed reference cuts.

DETAILED DESCRIPTION

Figure 1:
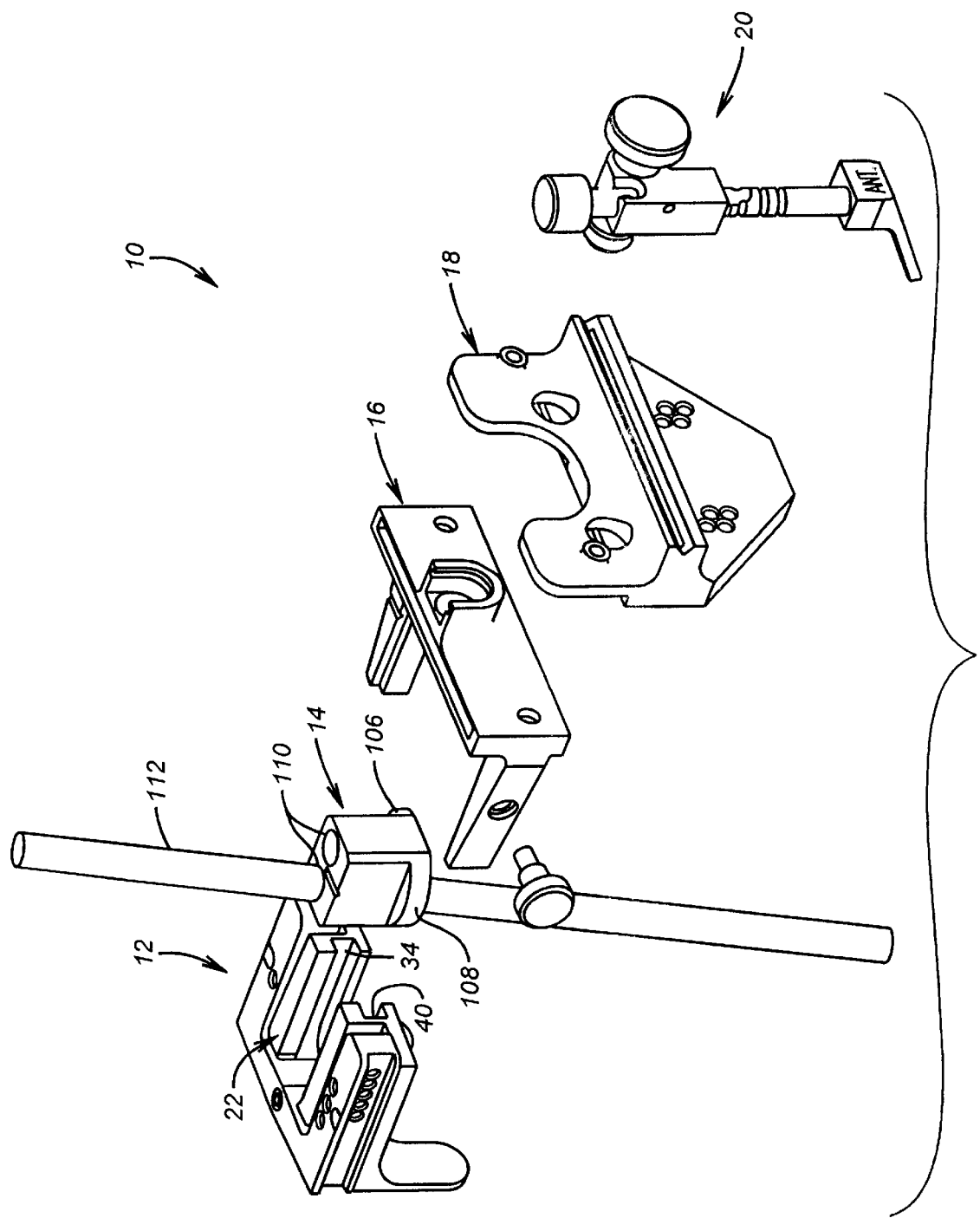
FIG. 1 is an exploded isometric view illustrating an embodiment of a distal femur sizing and resecting device.
Figure 2:
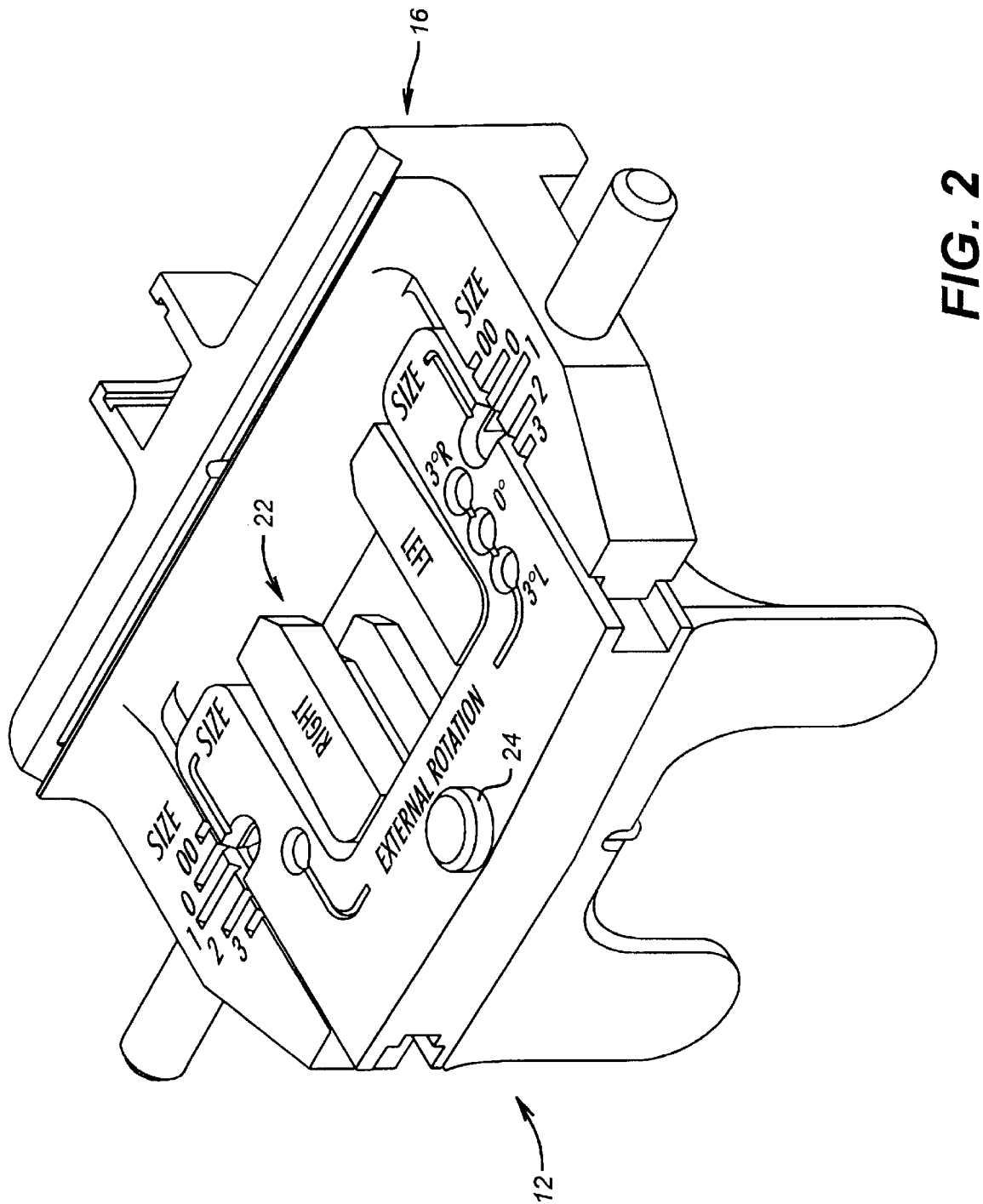
FIG. 2 is an isometric view illustrating an embodiment of assembled portions of the device.

A device for distal femur sizing and resection is generally designated 10 in FIG. 1, and includes a sizer member 12, a slide member, referred to as a slide stone 14, a femoral cut guide 16, a distal cut guide 18, and a reference device 20. Sizer member 12, FIG. 2, includes a slide member receiver 22, connected to sizer member 12 at a pivot point 24 to permit slide member receiver 22 to pivot relative to sizer member 12.

Figure 3:
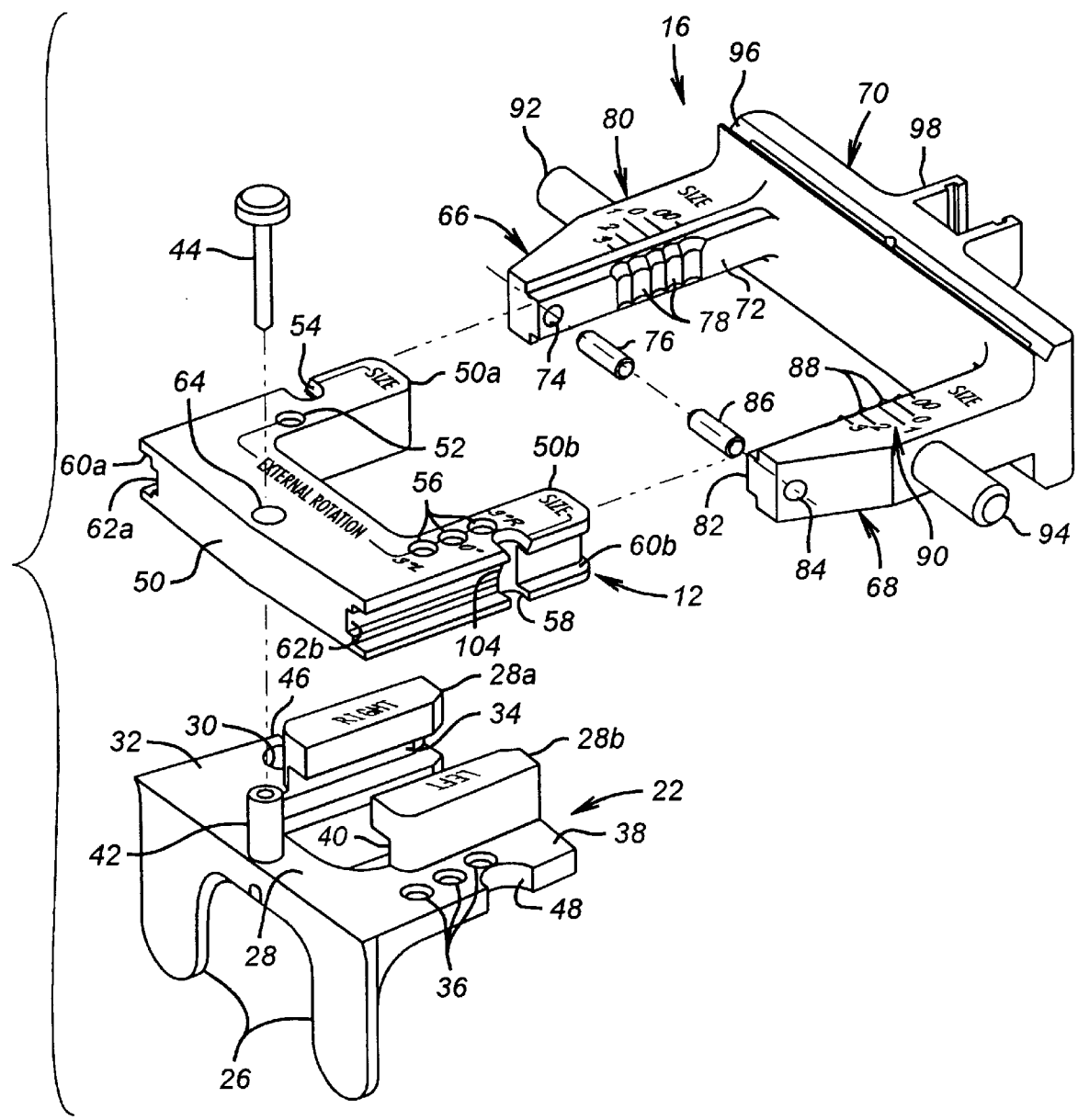
FIG. 3 is an exploded isometric view illustrating an embodiment of separated portions of the device.

Slide member receiver 22, FIG. 3, is generally L-shaped including a pair of paddles 26 and a bifurcated extension 28 including a first portion 28a and a second portion 28b. First portion 28a includes a rotation aperture 30 formed in a flange 32, and a slide member receiver groove 34. Second portion 28b includes a plurality of rotation apertures 36 formed in a flange 38, and a slide member receiver groove 40. A pivot pin receiver 42 extends from slide member receiver 22. Additionally, flange 32 includes a size scale notch 46 and flange 38 includes a size scale notch 48.

Sizer member 12 is generally u-shaped including a bifurcated portion 50 having a first portion 50a and a second portion 50b. First portion 50a includes a rotation aperture 52 and a size scale notch 54. Second portion 50b includes a plurality of rotation apertures 56 and a size scale notch 58. Sizer member 12 also includes a pair of opposed external grooves 60a and 60b and a pair of opposed pin grooves 62a and 62b formed in external grooves 60a and 60b, respectively. A pivot pin 44 is insertable into an aperture 64 formed in sizer member 12.

Figure 4:
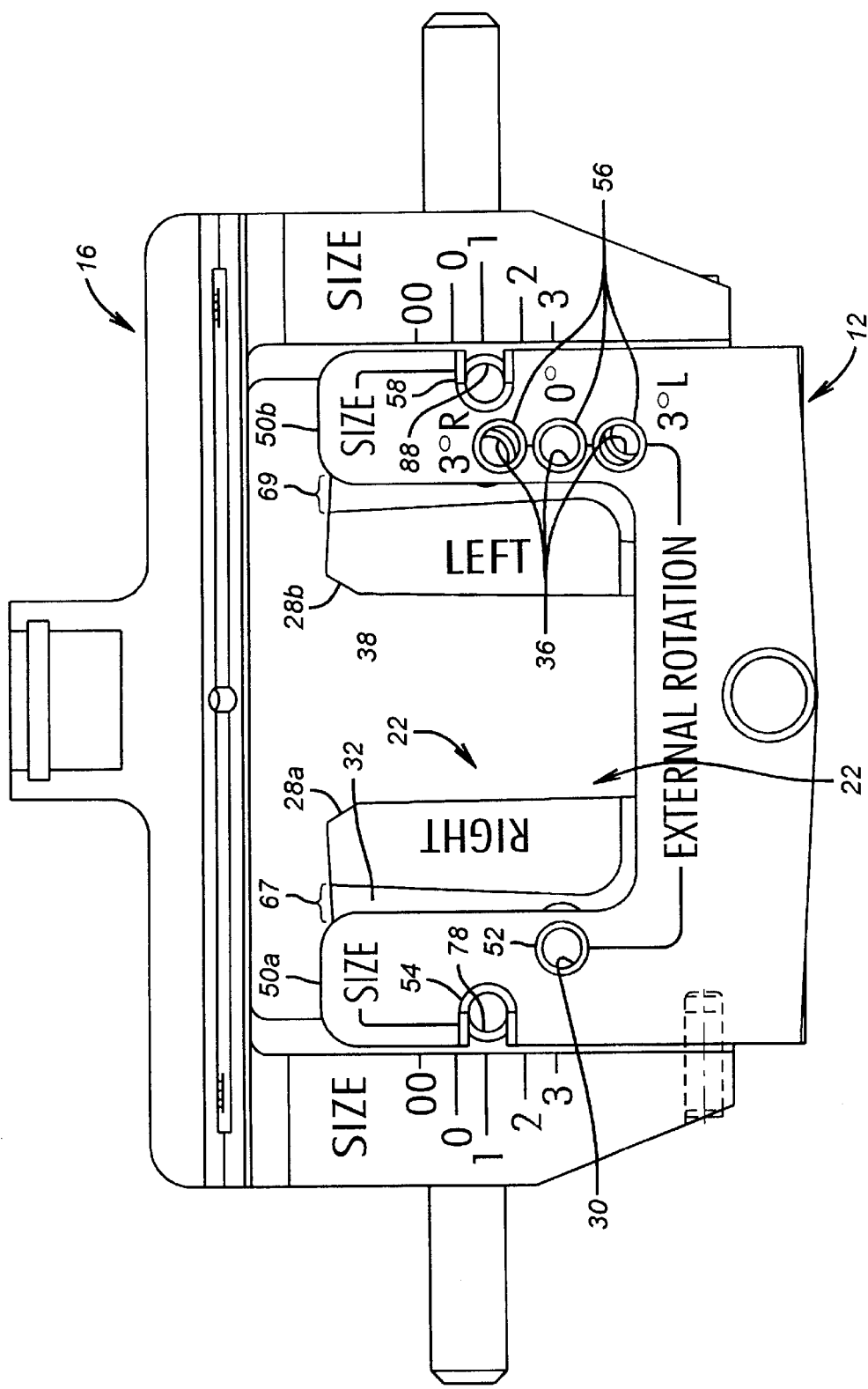
FIG. 4 is a top view illustrating an embodiment of assembled portions of the device.

When assembled, pivot pin receiver 42 extends through aperture 64 and receives pivot pin 44. First portion 28a, FIG. 4, and second portion 28b nest between first portion 50a and second portion 50b, respectively. A gap 66 between first portion 28a and 50a, and a gap 68 between second portion 28b and 50b, permits pivotal movement between sizer member 12 and slide member receiver 22. Also, such pivotal movement permits flange 32 to move relative to first portion 50a and simultaneously permits flange 38 to move relative to second portion 50b. This permits alignment between rotation apertures 30 and 52, and alignment between rotation apertures 36 and 56. Also, size scale notch 54, FIGS. 3 and 4, is aligned with size scale notch 46, and size scale notch 58 is aligned with size scale notch 48.

Figure 5:
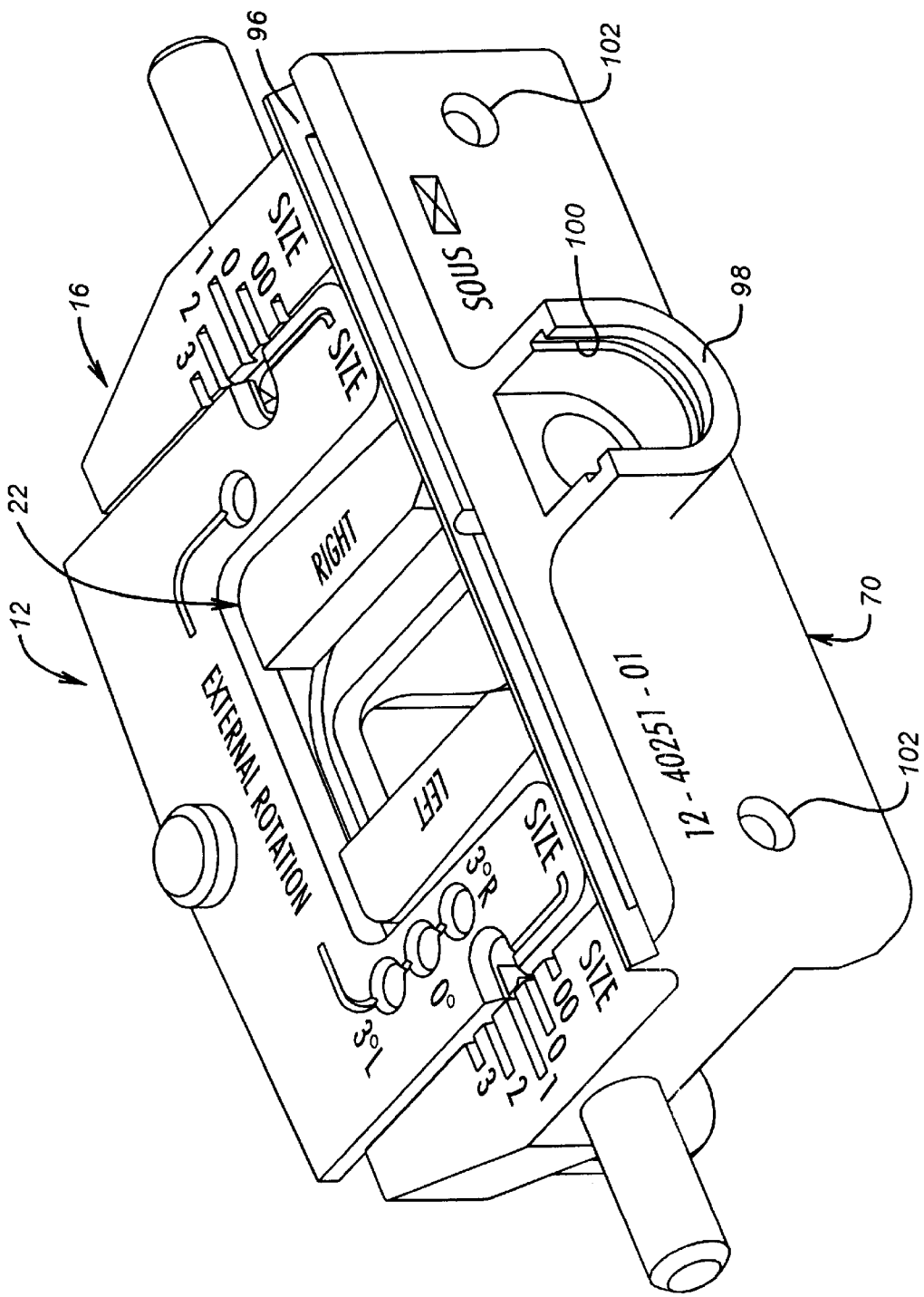
FIG. 5 is an isometric view illustrating an embodiment of assembled portions of the device.

Femoral cut guide 16, FIG. 3, is generally u-shaped including a first sizer extension 66, a second sizer extension 68 and a flange 70. First sizer extension 66 includes an internal tongue 72, an aperture 74 for receiving a pin 76 to protrude therefrom, a plurality of scalloped size scale notches 78, and a readable size index 80, including indices of 00, 0, 1, 2 and 3. Second sizer extension 68 includes an internal tongue 82, opposite tongue 72, an aperture 84 for receiving a pin 86 to protrude therefrom, a plurality of scalloped size scale notches 88, and a readable size index 90, including indices of 00, 0, 1, 2 and 3. Also, a pair of extensions 92 and 94 extend in opposite directions from extensions 66 and 68, respectively. Flange 70 includes a femoral cut guide slot 96, see also FIG. 5, a first femoral receiver 98 including a groove 100 formed therein, and a second femoral receiver including a pair of femoral temporary pin apertures 102. When assembled, FIG. 3, tongues 72 and 82 slide within grooves 60a and 60b, respectively. Pins 76 and 86 slide within grooves 62a and 62b, respectively, and capture sizer member 12 for limited sliding motion with femoral cut guide 16 by means of a stop 104, only one of which is visible in FIG. 3.

Figure 6:
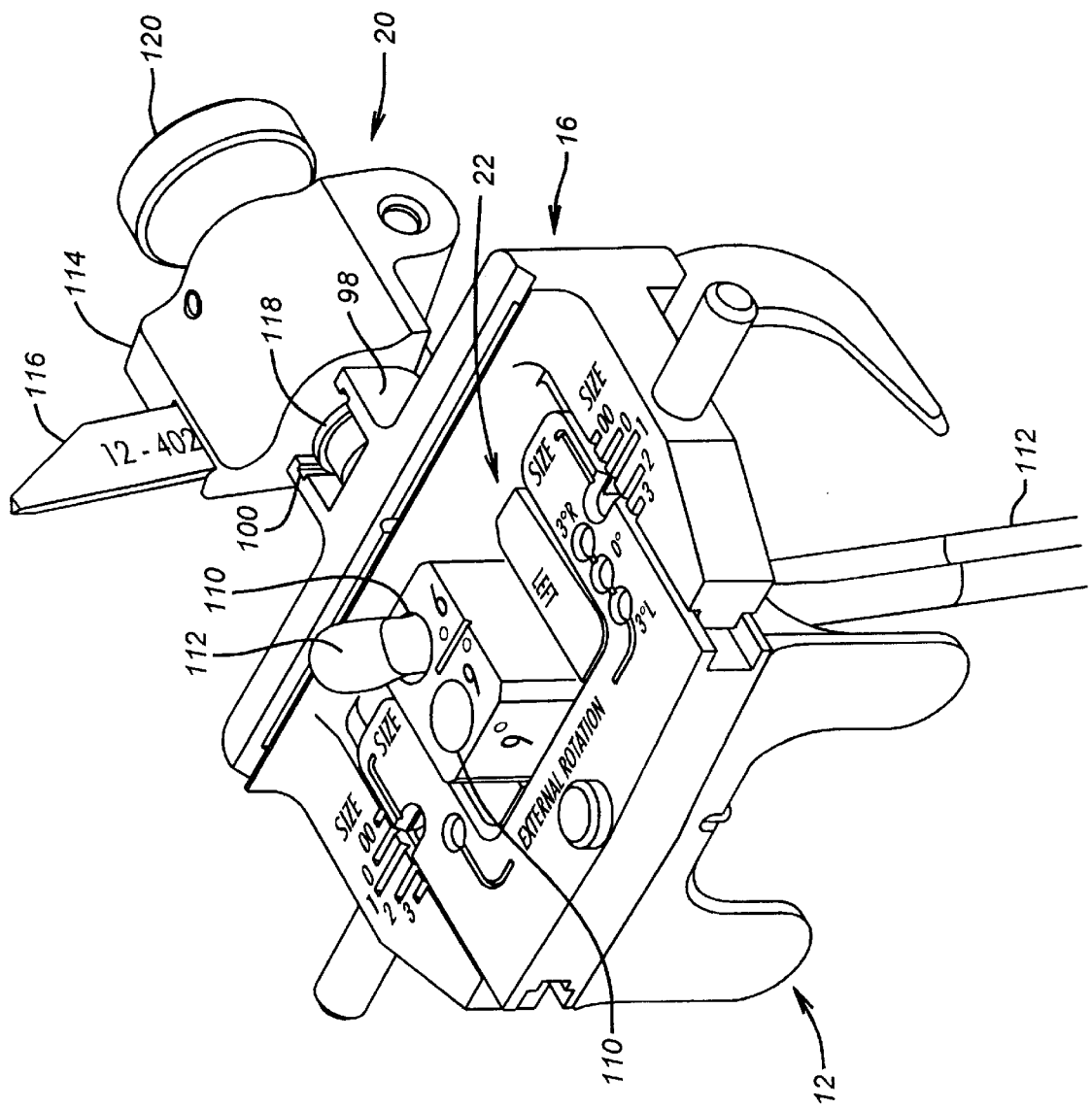
FIG. 6 is an isometric view illustrating an embodiment of assembled portions of the device.

Slide stone 14, FIG. 1, is slidably received by slide member receiver 22 due to engagement of a pair of opposed tongues 106 and 108 on slide stone 14, being slidably received in grooves 34 and 40, respectively. Also, slide member 14, includes a pair of angled apertures 110 formed therein for receiving an intramedullary rod 112, see also FIG. 6. Reference device 20 includes a stylus holder 114 and a posterior referencing stylus 116, FIGS. 6 and 7, adjustably mounted in stylus holder 114. A tongue portion 118, on stylus holder 114 is inserted in groove 100. Rotation of a threaded adjustable retainer 120 mounted in stylus holder 114, advances retainer 120 toward receiver 98, thus forcibly securing tongue 118 in groove 100. Adjustment of stylus 116, FIG. 7, in stylus holder 114, is accomplished by reciprocal movement of a resiliently mounted lock plunger 121 which engages one of several scalloped notches 122 formed in stylus 116, thus permitting stylus 116 to be moved within a slot 124 in stylus holder 114, in directions indicated by an arrow designated D1, so that a graduated size scale 126, on stylus 116, including indices 00, 0, 1, 2, 3, is movable relative to a size scale marker 128 on stylus holder 114.

Figure 7:
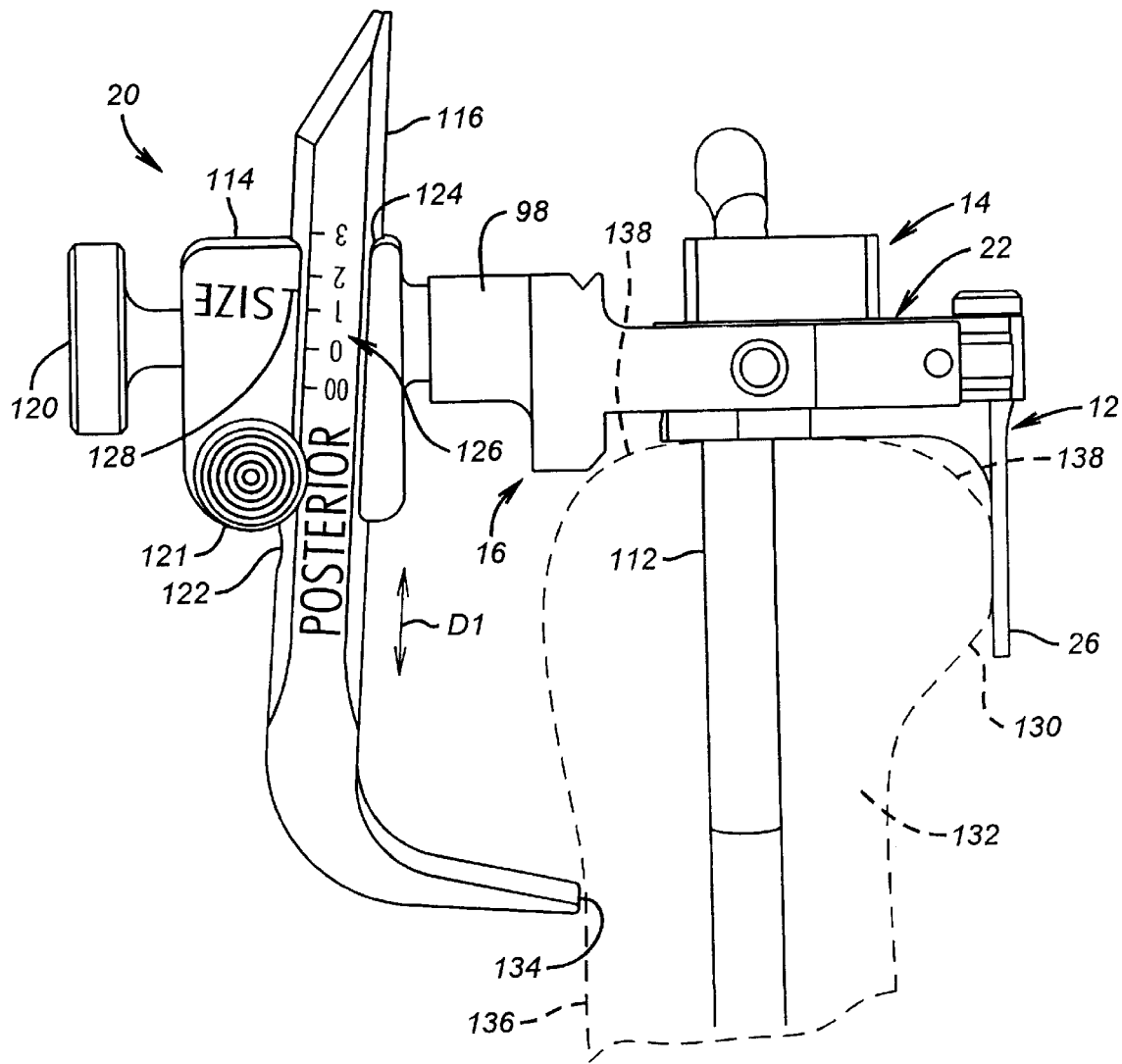
FIG. 7 is a side view illustrating an embodiment of assembled portions of the device engaged with a distal femur.

In the configuration generally illustrated in FIG. 7, paddles 26 engage posterior condyles 130 of a distal femur 132. A tip end 134 of stylus 116 is adjusted in the directions indicated by arrow D1 to engage anterior surface 136 of distal femur 132. A distal surface 138 of distal femur 132 abuts against slide member receiver 22. Intramedullary rod 112 is within the intramedullary canal of distal femur 132. Pivotal rotation of slide stone 14 with slide member receiver 22, sliding adjustment of sizer member 12 relative to femoral cut guide 16, and adjustment of stylus 116 in stylus holder 114, all done concurrently, will provide matched size readings on the reference device 20 and the sizer member 12, such that a prothesis size is indicated.

Figure 7A:
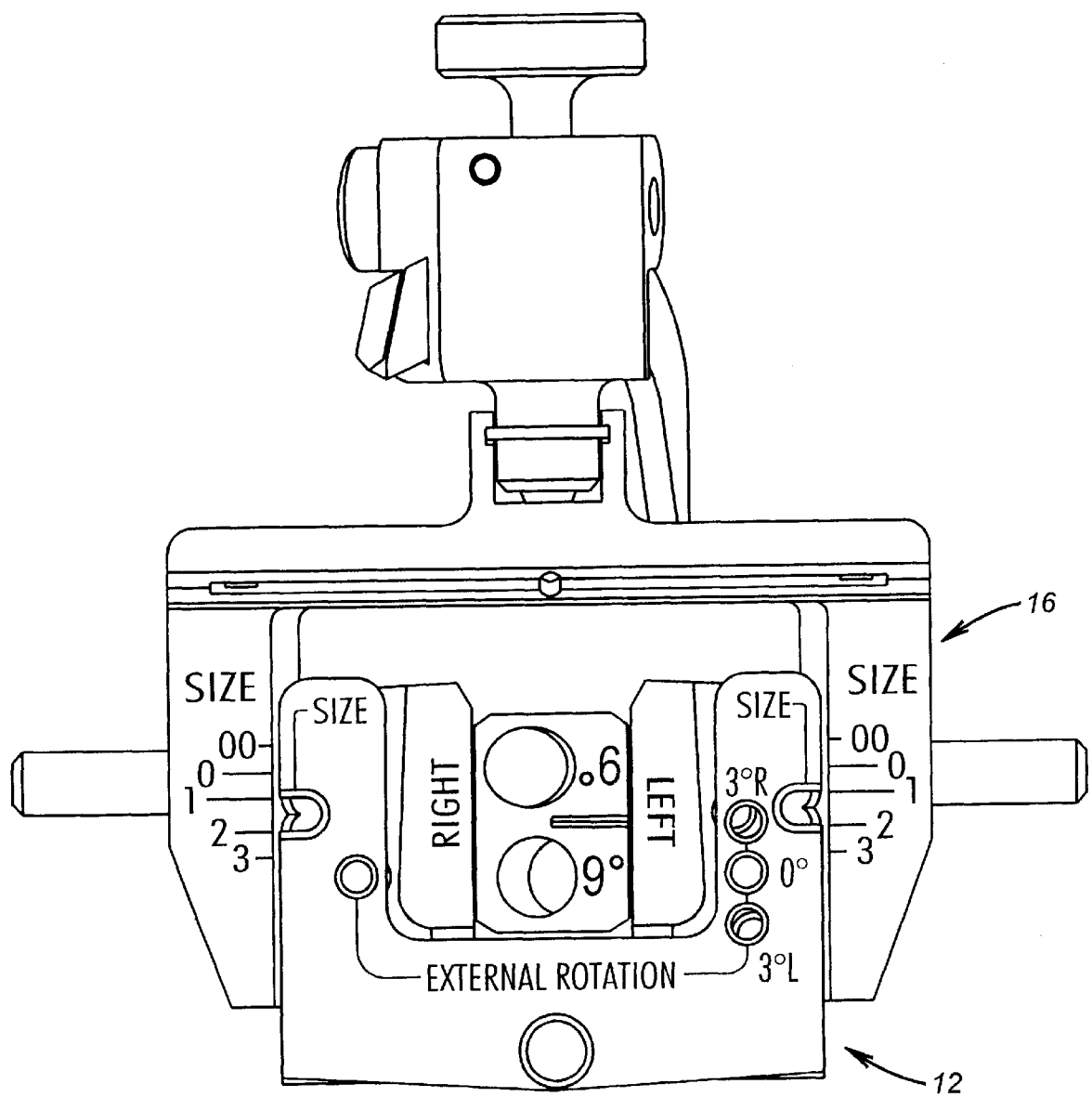
FIG. 7A is a plan view illustrating an embodiment of a sizer member and a femoral cut guide indicating a half size reading.
Figure 7B:
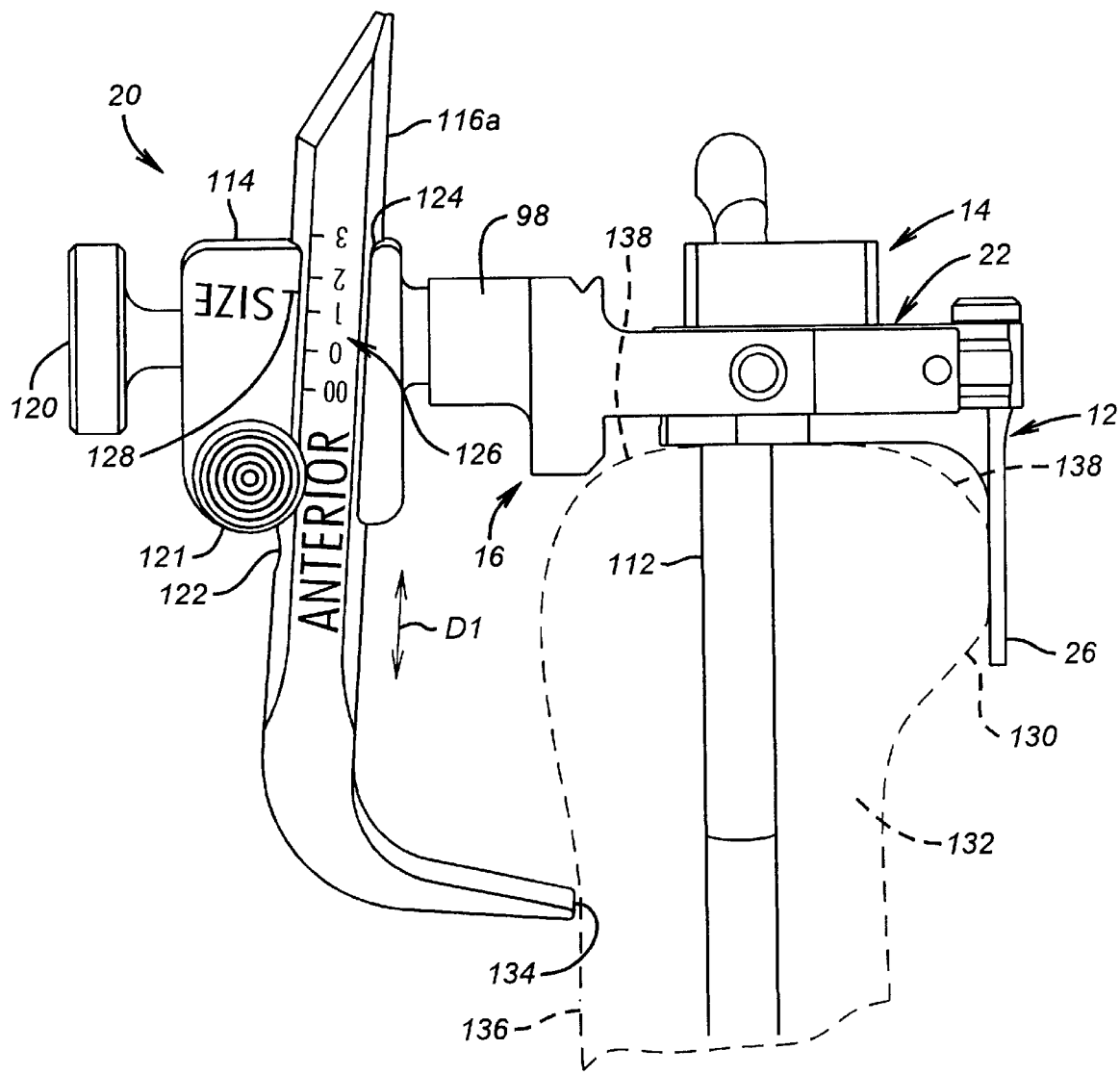
FIG. 7B is a side view illustrating an embodiment of assembled portions of the device engaged with the distal femur.
Figure 7C:
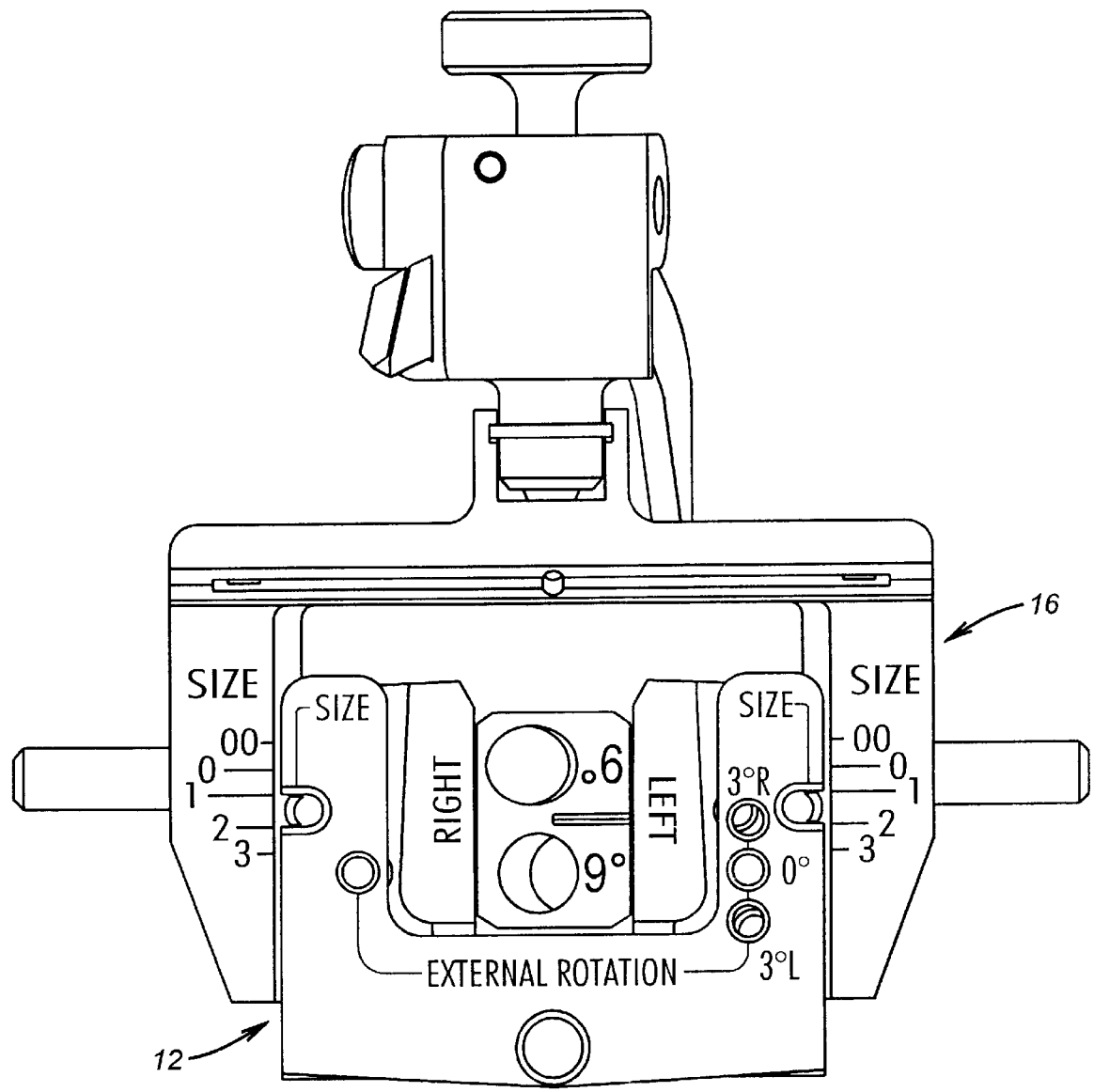
FIG. 7C is a plan view illustrating an embodiment of the sizer member and femoral cut guide indicating a prothesis size of 1.

In the event that a half size reading is obtained, e.g. the reading is half way between the 1 and 2 indices on the stylus 116, as illustrated in FIG. 7, and on the femoral cut guide 16, FIG. 7A, an anterior reference stylus 116a may replace the posterior reference stylus 116, see FIG. 7B. The size of anterior reference stylus 116a is greater than the size of posterior reference stylus 116, i.e. the tip end 134a of stylus 116a has a longer extension than the tip end 134 of stylus 116. The difference in length is 1.5 mm which relates to one-half of an implant size. Therefore, an adjustment of stylus 116a in directions indicated by arrow D1 will move tip 134a into engagement with anterior surface 136 of distal femur 132. This will result in a further concurrent sliding adjustment of sizer member 12 relative to femoral cut guide 16, and an adjusted matched size reading on the reference device 20 and the sizer member 12, such that a prothesis size, e.g. size 1, is indicated on stylus 116a, and on the femoral cut guide 16, FIG. 7C. By switching to an anterior referencing stylus, the result is that more bone will be removed from the posterior condyles 130 when chamfer cuts are made in a subsequent procedure. The surgeon can adjust the distal cut, discussed below, to remove an equal amount of bone from the distal surface 138, to compensate for the bone removed from the posterior condyles 130. This results in balanced joint bone cuts.

Figure 8:
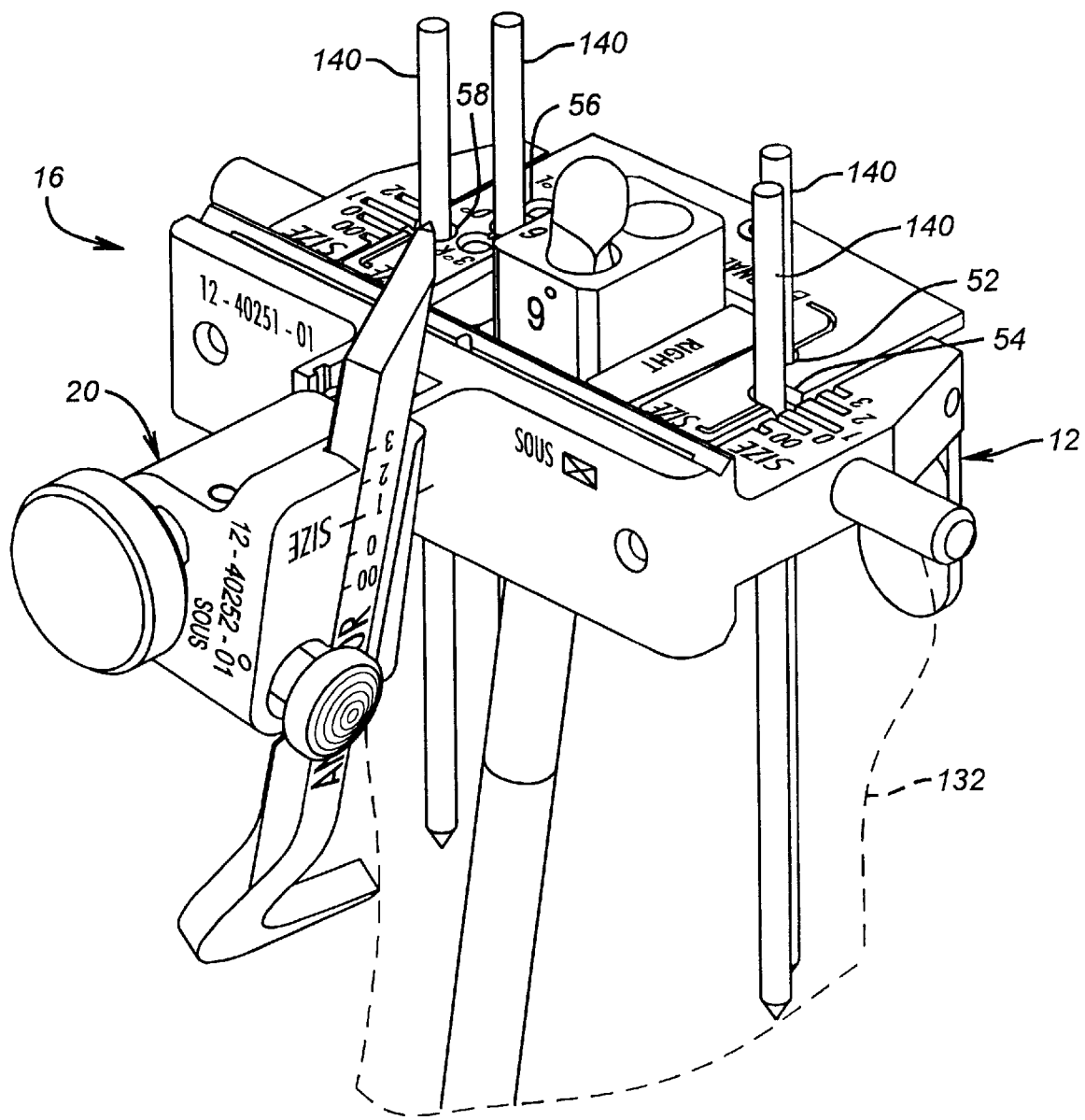
FIG. 8 is an isometric view illustrating an embodiment of assembled portions of the device engaged with the distal femur.
Figure 9:
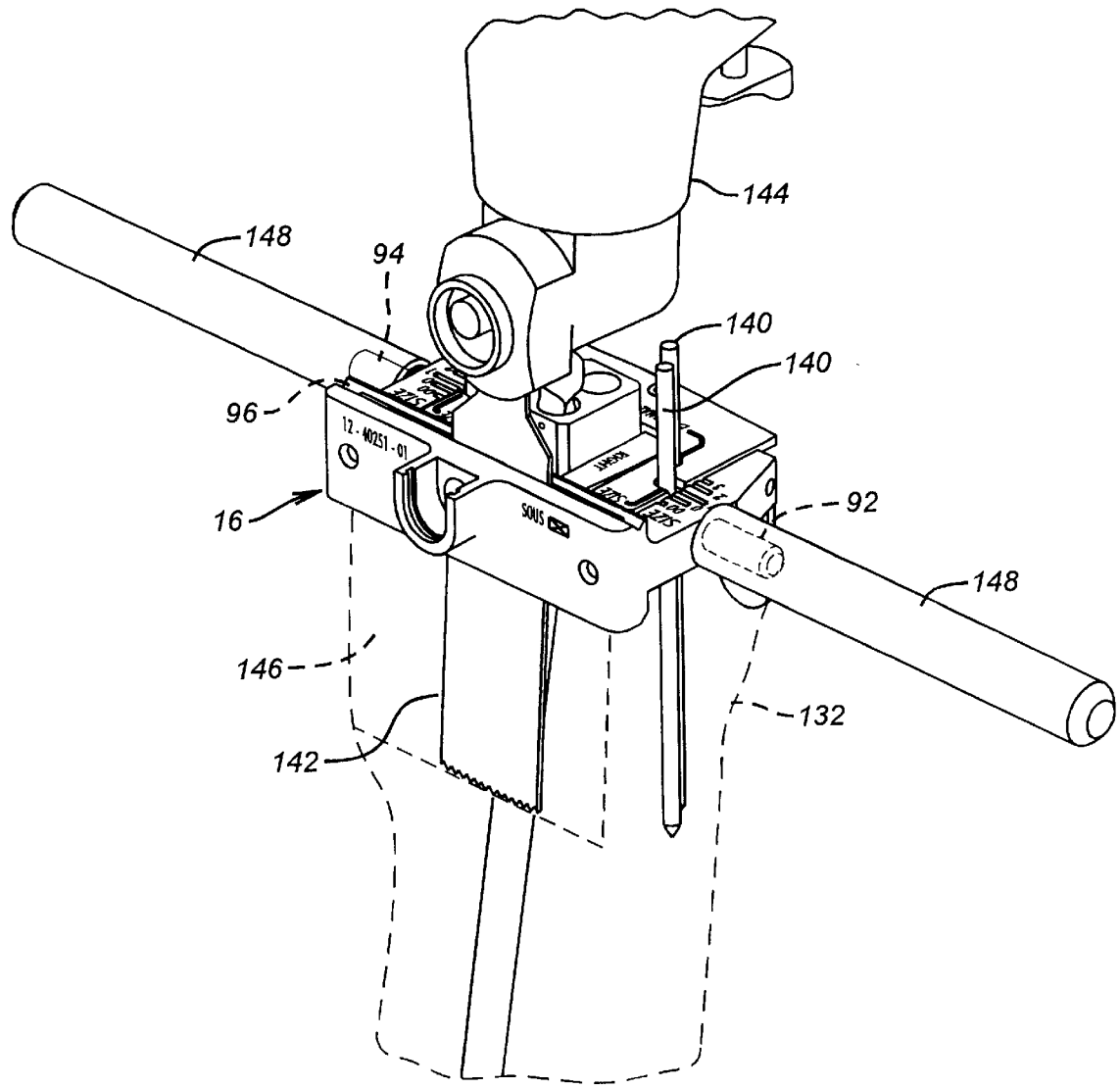
FIG. 9 is an isometric view illustrating a reference cut being made using an embodiment of assembled portions of the device engaged with the distal femur.

The readings on sizer member 12 may be retained by inserting pins 140 into distal femur 132, FIG. 8. Pins 140 insert through aligned ones of rotation apertures 56 and 36, FIGS. 3 and 4, rotation apertures 52 and 30 when aligned, aligned ones of size scale notches 54, 78 and 46 and aligned ones of size scale notches 58, 88 and 48 to create a macro lock. Thus, femoral cut guide 16 is secured to distal femur 132 and reference device 20 is removed, FIG. 9, to permit a saw blade 142 of a surgical cutting instrument 144 to be inserted through guide slot 96 to thus provide an anterior reference surface 146. Handles 148 are secured to extensions 92 and 94 to provide for hand-held stabilizing of femoral cut guide 16 during the cutting operation.

Figure 10:
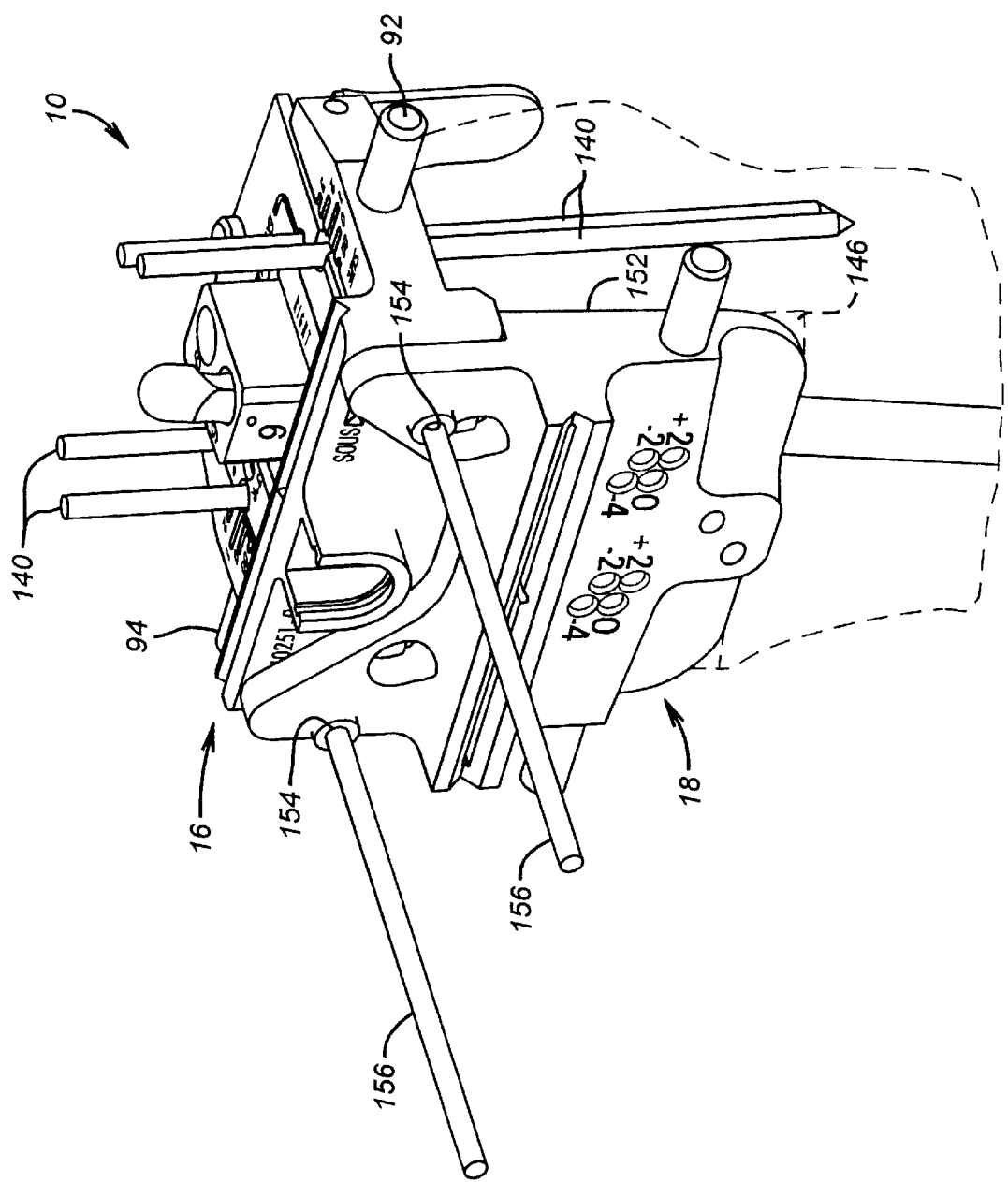
FIG. 10 is an isometric view illustrating an embodiment of assembled portions of the device engaged with the distal femur.
Figure 11:
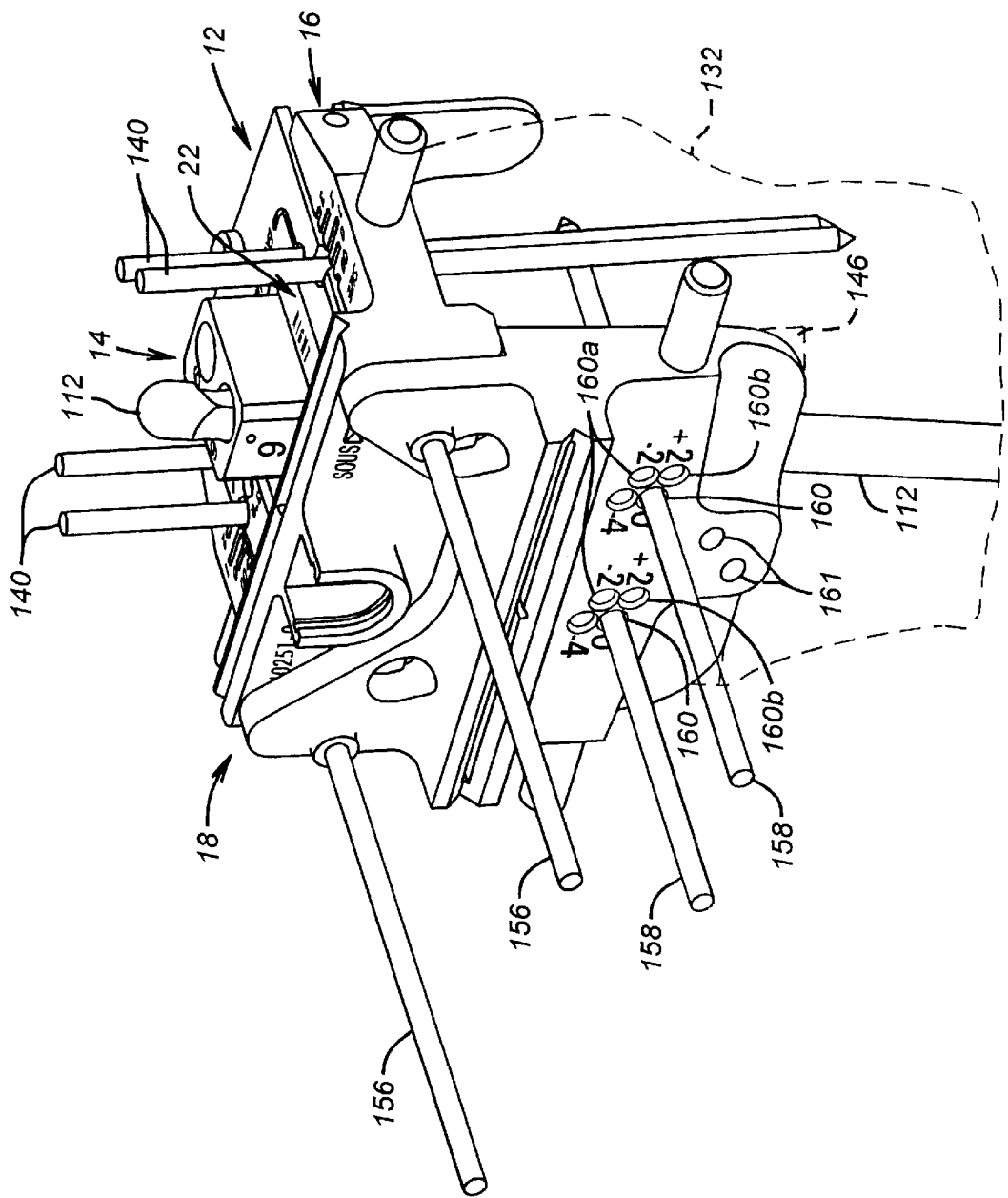
FIG. 11 is an isometric view illustrating an embodiment of assembled portions of the device engaged with the distal femur.

The device 10, FIG. 10, also provides for assisting in accurately locating and cutting a distal femoral surface. This is accomplished by first removing the handles 148 from extensions 92 and 94, and engaging the distal cut guide 18 with the femoral cut guide 16 and abutting a planar surface 152 of distal cut guide 18 with anterior reference surface 146. Also, distal cut guide 18 includes a pair of temporary pin apertures 154 which align with femoral temporary pin retaining apertures 102 (see also FIG. 5). A pair of temporary pins 156, inserted through aligned apertures 154 and 102, FIG. 10, temporarily retain distal cut guide 18 engaged with femoral cut guide 16. A plurality of distal attachment pins 158, FIG. 11, are inserted through a plurality of selected distal attachment pin apertures 160 in distal cut guide 18, and driven into distal femur 132 through the anterior reference surface 146, and temporary pins 156 are removed. It is at this point that the surgeon can make an adjustment to the distal cut, as mentioned above, to remove an equal amount of bone from distal surface 138 to compensate for the bone to be removed from the posterior condyles 130, to provide the balanced joint bone cuts.

Routinely, the surgeon will insert attachment pins 158 through the O referencing pin apertures 160 to allow for a visual assessment of the amount of bone to be removed distally, to determine whether to adjust for the removal of more or less bone, the purpose being to balance the amount of bone removed, both distally and posteriorly from the femur, which will result in equal flexion and extension when the implant is positioned on the bone. For example, if the procedure began using the posterior referencing stylus 116, resulting in a half size reading, followed by a change to the anterior referencing stylus 116a as described above, the position of distal cut guide 18 may be adjusted downwardly to remove more bone distally. This is accomplished by sliding the distal cut guide 18 from the attachment pins 158, aligning pins 158 with a pair of −2 pin apertures 160a, and sliding distal cut guide 18 on pins 158 toward anterior reference surface 146. Alternatively, if the procedure began using the anterior referencing stylus 116a, followed by a change to the posterior referencing stylus 116, the position of distal cut guide 18 may be adjusted upwardly to remove less bone distally, by following the procedure above but aligning the pins 158 with a pair of +2 pin apertures 160b. If it is not necessary to change from one stylus to another, then pins 158 may remain in the O reference pin apertures 160. Additional pin apertures 161, are provided at an angle in distal cut guide 18, if it is desired to use additional attachment pins to create a macro lock.

Pins 140 along with femoral cut guide 16 are also removed including sizer member 12, slide receiver member 22, slide stone 14 and intramedullary rod 112. This results in distal cut guide 18, FIG. 12, remaining secured to the distal femur 132 by distal attachment pins 158. As a result, the saw blade 142 of the surgical cutting instrument 144 may be inserted through a distal cut guide slot 160 provided in distal cut guide 18, for making the distal femoral cut to establish a distal reference surface 162. Following the cutting operation, distal guide 18 is removed from distal femur 132 by removing distal attachment pins 158, resulting in the establishment of anterior reference surface 146, FIG. 13, and distal reference surface 162 as a first and second locating datum for a chamfer speed block to perform the required multiple chamfer cuts on distal femur 132.

In operation, the adjustable sizer cut guide device, including the first readable scale, is assembled such that the sizer member, the femoral cutting guide and the slide stone are slidably interconnected. The slide stone is selected according to the valgus angle of the patient's anatomy. The slide stone receives the intramedullary rod which is inserted into the patient's intramedullary canal, and the adjustable sizer cut guide device is positioned in engagement with the distal and posterior surfaces of the distal end of the femur.

An adjustable referencing device, including the second readable scale, is removably attached to the adjustable sizer cut guide device. The adjustable sizer cut guide device and the adjustable referencing device are concurrently adjusted until the first readable scale and the second readable scale provide a matching reading which corresponds to an implant size. Metal pins are driven through openings in the adjustable sizer cut guide device so that the device is secured to the distal femur and positioned for desired size and rotation. The adjustable referencing device is removed from the adjustable sizer cut guide device. A saw blade of a surgical cutting instrument is inserted into the anterior reference cut guide slot which is provided in the femoral cutting guide, and the anterior femoral reference cut is formed in the anterior surface of the distal femur.

The distal cut guide is positioned against the surface of the anterior reference cut and temporarily attached to the femoral cutting guide with metal positioning pins. Metal pins are also driven through the zero reference holes in the distal cut guide and into the distal femur and the positioning pins are removed. The intramedullary rod is removed from the intramedullary canal and from the slide stone. The metal pins which secure the adjustable sizer cut guide device are removed from the distal femur and the adjustable sizer cut guide device is removed from its position on the distal femur. A saw blade of a surgical cutting instrument is inserted into the distal cut guide slot which is provided in the distal cut guide, and the distal femoral cut is formed in the distal surface of the distal femur. The metal pins securing the distal cut guide to the distal femur are removed and the distal cut guide is removed. The distal femur includes the anterior femoral reference cut and the distal femoral cut. A speed block, or the like, is positioned and secured on the distal femur in a known manner to provide for the anterior and posterior cuts to be made and to provide for the anterior and posterior chamfer cuts to be made.

As a result, one embodiment provides a device for distal femur sizing and resection including a sizer member, a slide member, movably mounted in the sizer member, and a femoral cut guide movably engaged with the sizer member. A first member and a second member are sequentially removably attachable to the femoral cut guide. The first member is a reference device attached to the femoral cut guide for referencing. The second member is a distal cut guide attachable to the femoral cut guide subsequent to removal of the reference device, to position the distal cut guide on the femur.

Another embodiment provides a femoral cut guide including a first retainer for retaining a removable reference device for referencing and a second retainer for retaining a removable distal cut guide subsequent to removal of the reference device, to position the distal cut guide on the femur.

As it can be seen, the principal advantages of these embodiments are that the device and the use thereof consolidate several time consuming steps into a compact procedure utilizing a multi-purpose instrument, to accurately locate and make the anterior femoral reference cut and the distal femoral reference cut.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. Apparatus for distal femur sizing and resection comprising:

a sizer member having a pair of opposed external grooves and having a slide member receiver pivotally mounted therein;

a slide member, movably mounted in the sizer member;

a femoral cut guide movably engaged with the sizer member;

a first member and a second member sequentially removably attachable to the femoral cut guide, the first member being a reference device attached to the femoral cut guide for referencing, and the second member being a distal cut guide attachable to the femoral cut guide subsequent to removal of the reference device, to position the distal cut guide on the femur.

2. The apparatus as defined in claim 1 wherein the sizer member includes a size scale notch formed therein and a sizer member rotation aperture formed therein.

3. The apparatus as defined in claim 2 wherein the slide member receiver includes a slide member rotation aperture formed therein, rotable into alignment with the sizer member rotation aperture.

4. The apparatus as defined in claim 2 wherein the femoral cut guide includes a pair of opposed internal tongues for sliding engagement with the opposed external grooves of the sizer member.

5. The apparatus as defined in claim 4 wherein the femoral cut guide includes a readable index adjacent the size scale notch of the sizer member.

6. The apparatus as defined in claim 5 wherein the femoral cut guide includes a femoral cut guide slot formed therein.

7. The apparatus as defined in claim 6 wherein the femoral cut guide includes a first femoral receiver for the reference device.

8. The apparatus as defined in claim 7 wherein the first femoral receiver includes a groove formed therein.

9. The apparatus as defined in claim 8 wherein the femoral cut guide includes a second femoral receiver.

10. The apparatus as defined in claim 9 wherein the second femoral receiver includes femoral temporary pin apertures.

11. The apparatus as defined in claim 10 wherein the distal cut guide includes a distal cut guide slot formed therein.

12. The apparatus as defined in claim 11 wherein the distal cut guide includes distal temporary pin apertures aligned with the femoral temporary pin apertures.

13. The apparatus as defined in claim 12 wherein the distal cut guide includes distal attachment pin apertures.

14. The apparatus as defined in claim 10 wherein the reference device includes a stylus holder and a stylus adjustably mounted in the stylus holder.

15. The apparatus as defined in claim 14 wherein the stylus holder includes an adjustable retainer threadably mounted therein.

16. The apparatus as defined in claim 15 wherein the stylus holder includes a tongue for engagement with the groove in the first femoral receiver.

17. The apparatus as defined in claim 14 wherein the stylus holder includes a size scale marker.

18. The apparatus as defined in claim 17 wherein the stylus includes a graduated size scale adjacent the size scale marker.

19. The apparatus as defined in claim 14 wherein the stylus includes index notches formed therein.

20. The apparatus as defined in claim 19 wherein the stylus holder includes a releasable lock member for engagement with the index notches.

21. The apparatus as defined in claim 20 wherein the releasable lock member is resiliently mounted in the stylus holder.

22. The apparatus as defined in claim 1 wherein the slide member receiver includes a pair of opposed slide member receiver grooves formed therein.

23. The apparatus as defined in claim 22 wherein the slide member includes an angled aperture formed therethrough for receiving an intramedullary rod.

24. The apparatus as defined in claim 23 wherein the slide member includes a pair of opposed slide member tongues for sliding engagement with the slide member receiver grooves.

25. A method of distal sizing and resection comprising the steps of:

slidably engaging a sizer member, a femoral cut guide and a slide stone into an adjustable sizer cut guide device including a first readable scale, the slide stone provided to receive an intramedullary rod inserted into the femur;

positioning the adjustable sizer cut guide device in engagement with a distal surface and a posterior surface of the distal femur;

attaching a first stylus, including a second readable scale, to the adjustable sizer cut guide device;

adjusting the adjustable sizer cut guide device and the first stylus until the first readable scale and the second readable scale provide a matching reading;

removing the first stylus in response to a half size reading being provided;

attaching a second stylus, including a third readable scale, to the adjustable sizer cut guide device;

adjusting the adjustable sizer cut guide device and the second stylus until the first readable scale and the third readable scale provide a matching reading equivalent to a prothesis size;

securing the adjustable sizer cut guide device to the femur with a first securing means;

removing the second stylus from the adjustable sizer cut guide device;

inserting a cutting instrument into an anterior reference cut guide slot provided in the adjustable sizer cut guide device;

cutting an anterior reference cut in the femur;

attaching a distal cut guide to the adjustable sizer cut guide device in engagement with the anterior reference cut;

securing the distal cut guide to the femur with a second securing means;

removing the adjustable sizer cut guide device, the intramedullary rod and the first securing means from the femur;

inserting a cutting instrument into a distal cut guide slot provided in the distal cut guide;

cutting a distal cut in the femur; and removing the distal cut guide and the second securing means from the femur.

\* \* \* \* \*